United States Patent [19]

Lawes

[11] Patent Number: 5,454,813
[45] Date of Patent: Oct. 3, 1995

[54] INTRAMEDULLARY INTERTROCHANTERIC FRACTURE FIXATION APPLIANCE

[75] Inventor: Peter Lawes, Maidenhead, United Kingdom

[73] Assignee: Howmedica International Inc., Shannon, Ireland

[21] Appl. No.: 149,167

[22] Filed: Nov. 8, 1993

Related U.S. Application Data

[63] Continuation of Ser. No. 902,103, Jun. 22, 1992, abandoned.

[30] Foreign Application Priority Data

Jun. 24, 1991 [GB] United Kingdom ............... 91135780

[51] Int. Cl.⁶ .................................................. A61B 17/56
[52] U.S. Cl. .................................................. 606/62; 606/64
[58] Field of Search ............................... 606/60, 61, 62, 606/63, 64, 65, 66, 67, 72, 73

[56] References Cited

U.S. PATENT DOCUMENTS

| | | | |
|---|---|---|---|
| 3,433,220 | 3/1969 | Zickel | 606/67 |
| 4,095,591 | 6/1978 | Graham | 606/66 |
| 4,103,683 | 8/1978 | Neufeld | 606/67 |
| 4,432,358 | 2/1984 | Fixel | 606/66 |
| 4,465,065 | 8/1984 | Gotfried | 606/65 |
| 4,612,920 | 9/1986 | Lower | 606/66 |
| 4,622,959 | 11/1986 | Marcus | 606/64 |
| 4,628,923 | 12/1986 | Medoff | 606/65 |
| 4,641,640 | 2/1987 | Griggs | 606/66 |
| 4,653,487 | 3/1987 | Maale | 606/62 |
| 4,657,001 | 4/1987 | Fixel | 606/66 |
| 4,697,585 | 10/1987 | Williams | 606/64 |
| 4,733,654 | 3/1988 | Marino | 606/64 |
| 4,776,330 | 10/1988 | Chapman | 606/65 |
| 5,007,910 | 4/1991 | Anapliotis | 606/66 |
| 5,032,125 | 7/1991 | Durham | 606/65 |
| 5,176,681 | 1/1993 | Lawes | 606/64 |

FOREIGN PATENT DOCUMENTS

| | | |
|---|---|---|
| 0251583 | 6/1987 | European Pat. Off. . |
| 0321170 | 6/1989 | European Pat. Off. . |
| 0441577 | 8/1991 | European Pat. Off. . |
| 2906068 | 6/1980 | Germany . |
| 8701164 | 6/1987 | Germany . |

OTHER PUBLICATIONS

Synthes 'Dynamic Implant Screw System' Institut Straumann AG, Waldenburg, CH, Bettlach, Ch Apr. 1989.
Blueprints of Howmedica's "Dennis Modified Zickel Rod" Sold in the 1970's.
Plus European Search Report for the corresponding EPO case.

*Primary Examiner*—Michael A. Brown
*Attorney, Agent, or Firm*—Peter C. Richardson; Lawrence C. Akers; Elizabeth O. Slande

[57] ABSTRACT

An intramedullary intertrochanteric fracture fixation appliance has an intramedullary rod having an angulated opening to receive a femoral neck screw. The femoral neck screw has a threaded portion at its proximal end of predetermined diameter. A locking element is provided which acts between the neck screw and the wall of the angulated opening to prevent relative rotation between the screw and the rod.

10 Claims, 6 Drawing Sheets

INTRAMEDULLARY INTERTROCHANTERIC FRACTURE FIXATION APPLIANCE

This is a continuation of application Ser. No. 07/902,103, filed on Jun. 22, 1992, now abandoned.

BACKGROUND OF THE INVENTION

1. Field of the Invention

This invention relates to an intramedullary intertrochanteric fracture fixation appliance.

2. Description of the Prior Art

Appliances of this kind are well known and are shown, for example, in the Applicants' European Patent Application No. 88311746.7 (Publication No. 0 321 170) and U.S. application Ser. No. 281,730 filed Dec. 9, 198, now U.S. Pat. No. 5,176,681.

Devices of this type can comprise an intramedullary rod having an angulated opening to receive a femoral neck screw which is sometimes provided in the form of a lag screw. The intramedullary rod is fitted into the intramedullary canal of the femur and the neck screw passes through the opening in the rod, through the neck of the femur and into the head. With this kind of device, it is possible to produce tension in the neck screw to pull the head and neck of the femur together, and means can be provided to prevent the screw from rotating both during this operation and in its final position. Alternatively, some surgeons prefer to merely lock the neck screw against rotation but not against axial movement, as required for the particular patient.

One type of intramedullary intertrochanteric fracture fixation appliance of this type is known as the "Gamma Nail". This has a lag screw with a nominal 12 mm diameter shaft which produces a close sliding fit in the angulated opening in the nail. The lag thread major diameter is also nominally 12 mm. Another type, including a sleeve, is shown in U.S. Pat. No. 5,032,125.

It is usual to prepare the femoral neck (to receive the lag screw) by inserting a guide wire (typically 2–3 mm diameter) along the chosen path center line first, and then any cannulated drills or taps can be run along the guide wire. With the present Gamma Nail procedure, the implant and instrumentation manufacture and the surgical technique are all demanding of extreme precision. Furthermore, the design concept assumes the guide wire will follow a straight path.

Contrary to the manufacturers intentions, some surgeons do not leave the guide wire in until the lag screw is fully in place. In some instances they avoid using the guide wire totally. In others, when they feel the 12 mm drill begin to bind, they remove the guide wire and then continue drilling. The present invention is intended to overcome some of the difficulties referred to above.

It is known to use lag screws in existing compression hip screw devices which employ a lateral bone plate. In these constructions the lateral bone plate is provided with a shaped bore in a projecting boss within which the lag screw can slide axially but not rotate. The boss forms an integral part of the lateral bone plate and the surgeon prepares a hole in the femur to accept it. These lag screws can typically have a 12 mm major diameter on the lag thread and about 8 mm diameter on the shaft. They are produced in slightly different designs and surgical instruments, for example, drills, taps and screw drivers, exist as standard for operating them.

A further advantage of the present invention therefore is that a lag screw for use in the invention defined herein can be of such a configuration that it could also be used with a lateral bone plate. Again, with this concept the parts of the present invention can be designed so that existing lag screws of this type can be used with it. Thus, when a hospital is already using compression hip screws, they could be provided with an intramedullary nail and sleeve which could be fully compatible with their existing lag screws, thus saving hospitals from stocking new instruments and implements. It will be appreciated that this advantage is not the prime requirement of the present invention but is an additional advantage.

The present invention is intended to simplify the procedure now used to implant the type of intramedullary fracture fixation appliance.

SUMMARY OF THE INVENTION

It is an object of the invention to provide an improved surgical technique for implanting an intramedullary fixator and to provide elements of the fracture fixation appliance necessary to accomplish this.

According to the present invention an intramedullary intertrochanteric fracture fixation appliance comprises an intramedullary rod having an angulated opening to receive a femoral neck screw having a threaded portion at its proximal end, and a locking element acting between the neck screw and the walls of the angulated opening to prevent rotation between the screw and the rod. If desired, a tension adjuster can be included for applying an adjustable tension to the neck screw to urge the proximal end of the neck screw towards the rod.

Preferably, the cross-sectional dimensions of the shank of the neck screw are less than the diameter of the threaded portion at the proximal end, and a longitudinally extending opening can be provided through the neck screw to receive a guide wire then in use. This new construction enables a new operative technique to be employed. Firstly, neither the lag thread drill nor the lag thread top, nor the lag screw itself, need have any 12 mm diameter surfaces. Secondly, the guide wire and nail become able to move slightly within the bone. The use of a drift and the removal of the alignment guide (after the wire is inserted) enables both the wire and the nail to hunt and minimize eccentricity and misorientation.

In one preferred construction, the neck screw can be fitted into the opening in the rod in two or more alternative relative rotational positions. The locking element comprises a locking member which is shaped to locate circumferentially on the shank of said screw and in said angulated opening, but with free axial movement in relation to both parts. Thus, the locking element can be provided by a sleeve which can slide over the screw shank and within the angulated opening. A benefit of adding the sleeve is that the length of engagement between the screw and the angulated opening can be increased from the present 17 mm (which is the diameter of the nail in present constructions) to 40 mm, which can be the length of the sleeve, and this increases the ease of sliding between the screw and nail as the bone fracture consolidates.

Preferably, the sleeve has an inner bore, the wall of which is shaped to provide first abutment surfaces which engage co-operating surfaces provided on the shank of said neck screw, and the outer surface of said sleeve is provided with second abutment surfaces to engage co-operating surfaces provided on the wall of the angulated opening in said intramedullary rod to prevent relative rotation between said neck screw and said rod. The tension adjuster can include an adjustable device for acting on the screw and bearing against the locking member, for example, the sleeve. Preferably the intramedullary rod includes means for attaching a removable fitting device.

These and other objects and features of the present invention will become apparent from the following detailed description considered in connection with the accompanying drawings, which disclose several embodiments of the invention. It is to be understood that the drawings are to be used for purposes of illustration only, and not as a definition of the limits of the invention.

BRIEF DESCRIPTION OF THE DRAWINGS

In the drawings, wherein similar reference characters denote similar elements throughout the several views.

DESCRIPTION OF THE PREFERRED EMBODIMENTS

Figure 1:
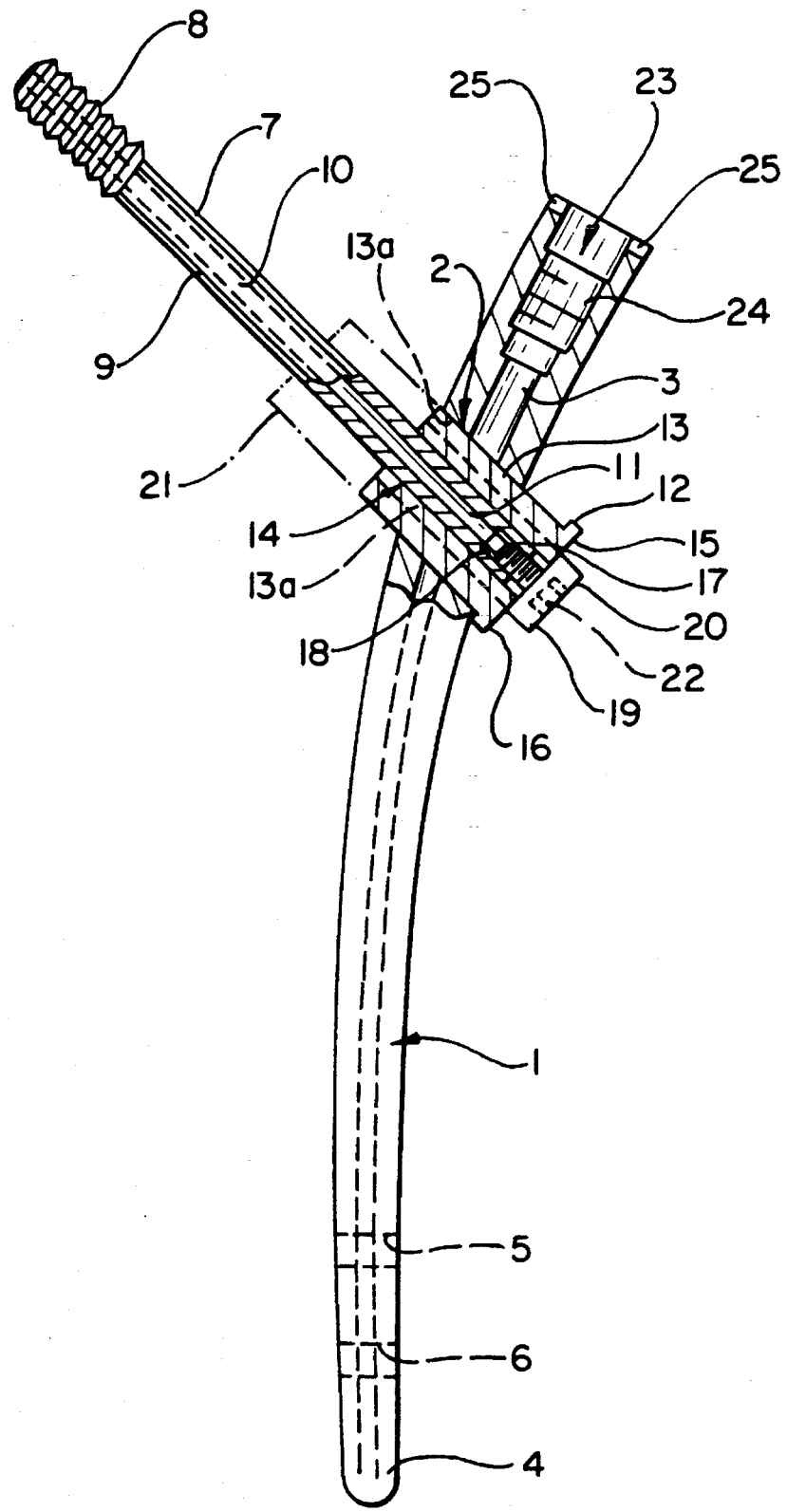
FIG. 1 is a part cross-sectional side elevation of an intramedullary intertrochanteric fracture fixation appliance according to the present invention.
Figure 2:
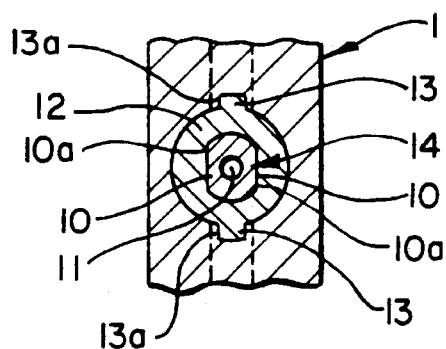
FIG. 2 is a cross-sectional end elevation on the line II—II of FIG. 1.

As shown in FIGS. 1 and 2, a first embodiment of an intramedullary intertrochanteric fracture fixation appliance according to the invention comprises an intramedullary rod 1 for introduction into the intramedullary canal of a femur. Rod 1 has an angulated opening 2 and a co-axial bore 3 which extends throughout its length. The distal end 4 of the rod is provided with two holes 5 and 6 to receive pins or screws (not shown) to fix and locate that end of the rod in the bone.

Located in angulated opening 2 is a femoral neck screw 7 in the form of a lag screw, the proximal end of which carries a coarse screw thread 8 and which has a shank 9 which is substantially circular but has flats 10 as most clearly shown in FIG. 2. Lag screw 7 is also provided with a longitudinally extending bore 11 through which a guide wire can extend during fitting.

In a typical embodiment, the diameter of angulated opening 2 in rod 1 can be 12 mm, and this is also the diameter of screw threaded portion 8 so that the neck screw can be passed through the angulated opening.

A means for locking neck screw 7 to prevent relative angular rotation in relation to rod 1 is provided by a locking member in the form of a sleeve 12, the inner bore 14 of which is shaped with first abutment surfaces in the form of flats 10a which are shaped to accommodate the shaped shank 9 of screw 7 and dimensioned so that it can slide on shank 9 but, due to flats 10, cannot rotate. The outer surface of the sleeve is substantially cylindrical but is formed with a pair of circumferentially spaced apart locking ridges 13 which act as second abutment surfaces. Similarly, the angulated opening 2 is provide with slots 13a which can cooperate with ridges 13 to prevent rotation of the sleeve. Thus, it will be seen that the cross-section of the outer surface of sleeve 12 is substantially the same as the cross-section of the opening 2, and the cross-section of inner bore 14 is substantially the same as the cross-section of shank 9 of neck screw 7.

The proximal end 15 of sleeve 12 is provided with a shoulder 16 so that the surgeon cannot push the sleeve through the nail 1 and out of the other side during fitting. The proximal end 17 of screw 7 is provided with an internal screw thread 18 to receive an adjusting screw 19, the head 20 of which is of larger diameter than bore 14 in the sleeve.

As shown in FIG. 1, the sleeve merely extends through rod 1, but if desired the length of the sleeve could be longer as shown in broken lines 21. A benefit of this is that the length of engagement between screw 7 and rod 1 can be increased. For example, if the diameter of rod 1 at angulated opening 2 is 17 mm, it can be increased to 40 mm by extending the length of the sleeve. This reduces the chance of the screw jamming in the rod as the bone fracture consolidates. It is believed that the slideability is related to engagement length when a static load rather than a walking-cycle loading pattern is applied. The sleeve and screw 7 are dimensioned so that when the screw is in position, the proximal end of the sleeve 12 extends beyond the proximal end of screw 7. The adjusting screw 19 is provided with a hexagonal socket 22 to receive an appropriately shaped screw driver to enable the screw to be rotated. Thus, the screw acts as a tension adjuster for applying an adjustable tension to the neck screw to urge the proximal end of the neck screw towards the rod when the locking means provided by the sleeve have been actuated. Head 20 of screw 19 acts on the distal end of the locking member provided by sleeve 15 to cause the effect referred to above.

The upper end of rod 1 has an enlarged bore 23 provided with a screw thread 24 and diametrically opposed radially extending slots 25 to receive a fitting device, for example, of the kind described in European Patent Application No. 88311746.7 (Publication No. 0 321 170).

The method of fitting the appliance is shown in the diagrammatic FIGS. 6 to 13 in which the same reference numerals are used to indicate similar parts as in FIGS. 1 and 2. In FIGS. 6 to 13, the femur to which the device is to be fitted is indicated by reference numeral 30 and a fitting device by reference numeral 31 which is provided with a tunnel locator 32 of known type.

Figure 6:
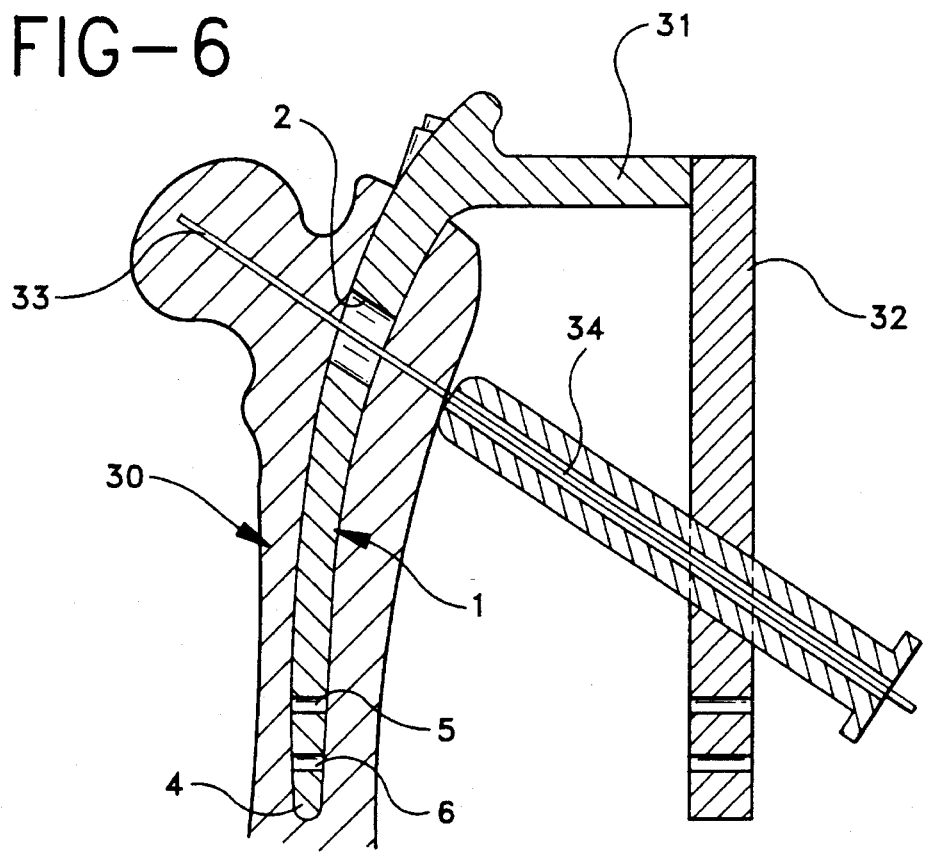
FIGS. 6 to 13 are diagrammatic illustrations showing the various stages during the implantation of the appliance according to the invention.
Figure 7:
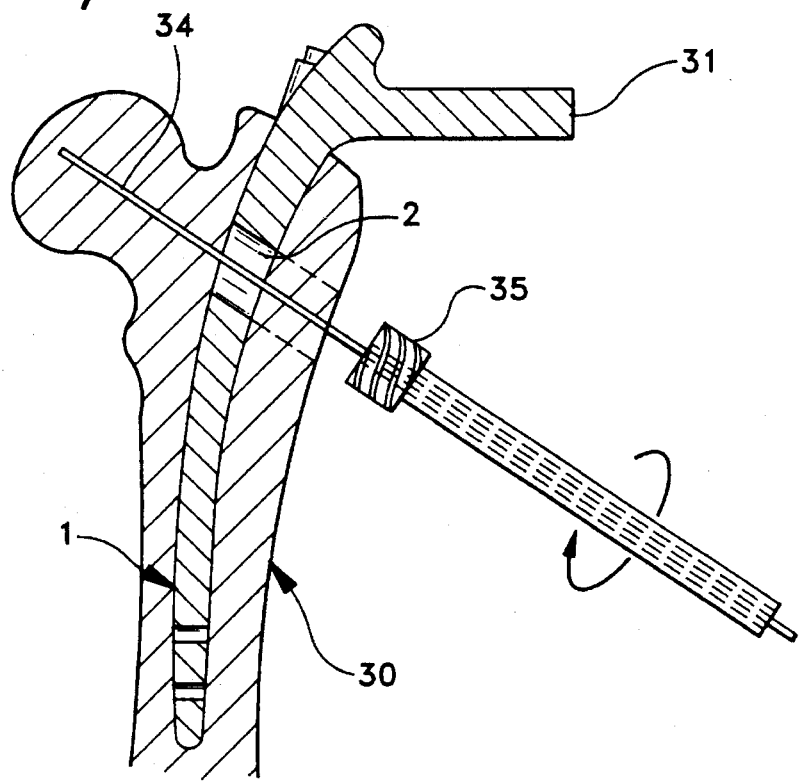

As shown in FIG. 6, rod 1 is installed according to normal procedures in the intramedullary canal of the femur 30. The fitting device 32 is then attached to the upper end of the nail 1 and the tunnel locator 32 is placed in position. A guide hole 33 is now drilled, again according to normal procedures, and a guide wire 34 is placed in position along the femoral neck center line. The tunnel guide 32 is now removed and a 12 mm diameter hole is drilled over the guide wire 34 using a drill 35 through the lateral cortex as shown in FIG. 7.

Figure 8:
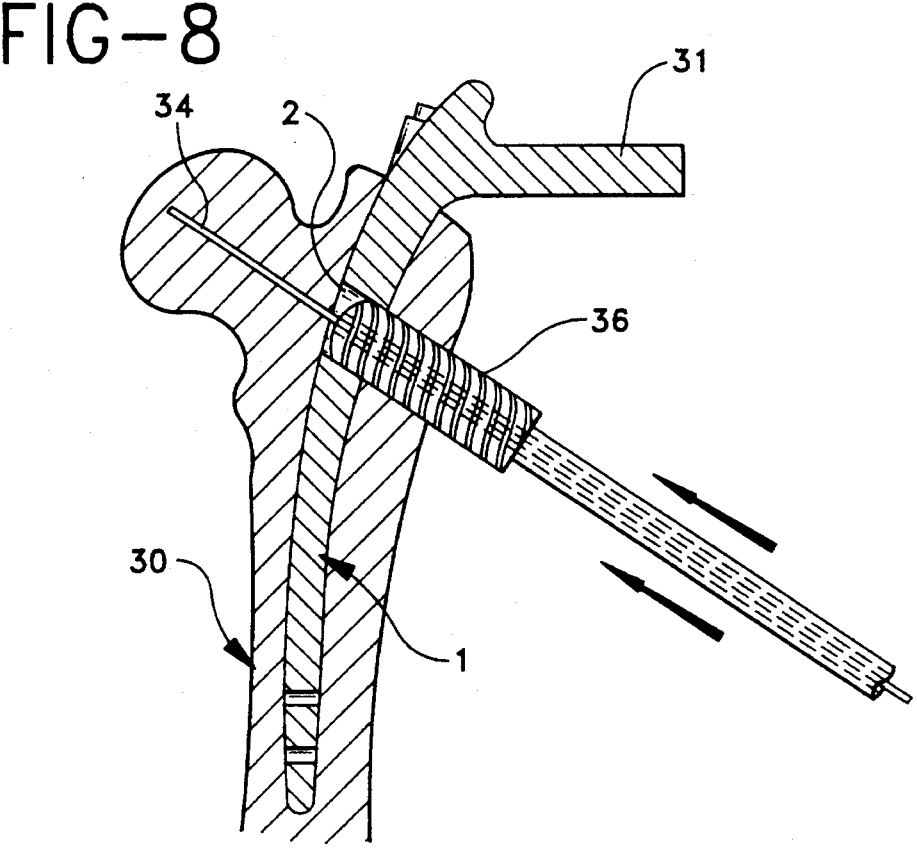
Figure 9:
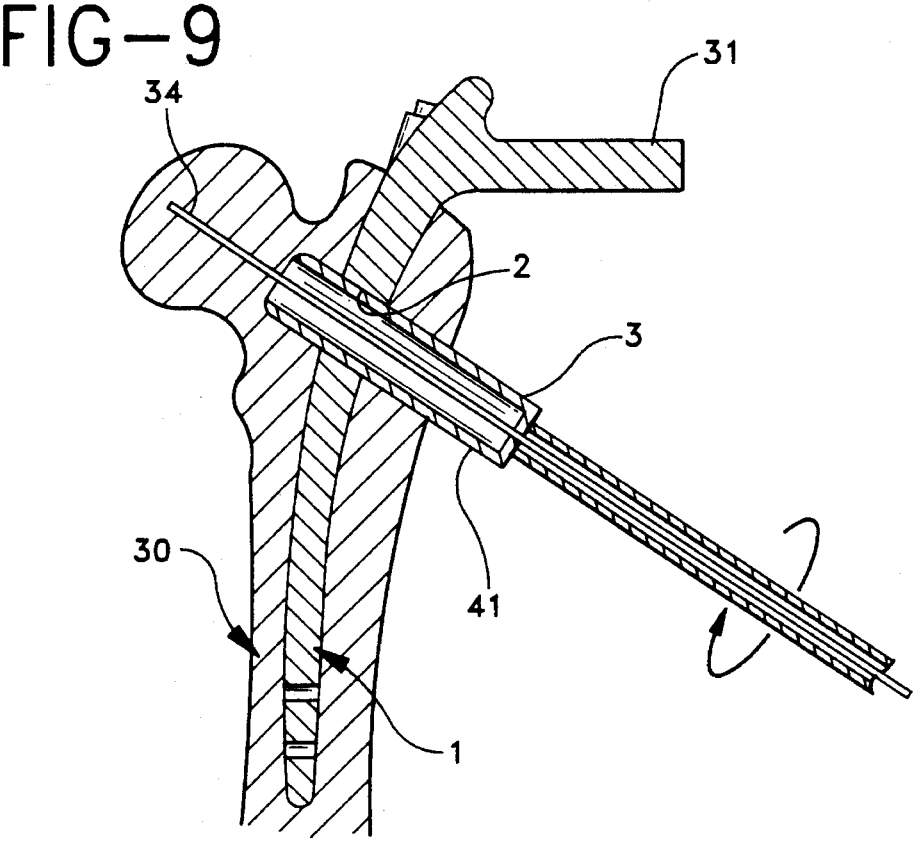
Figure 10:
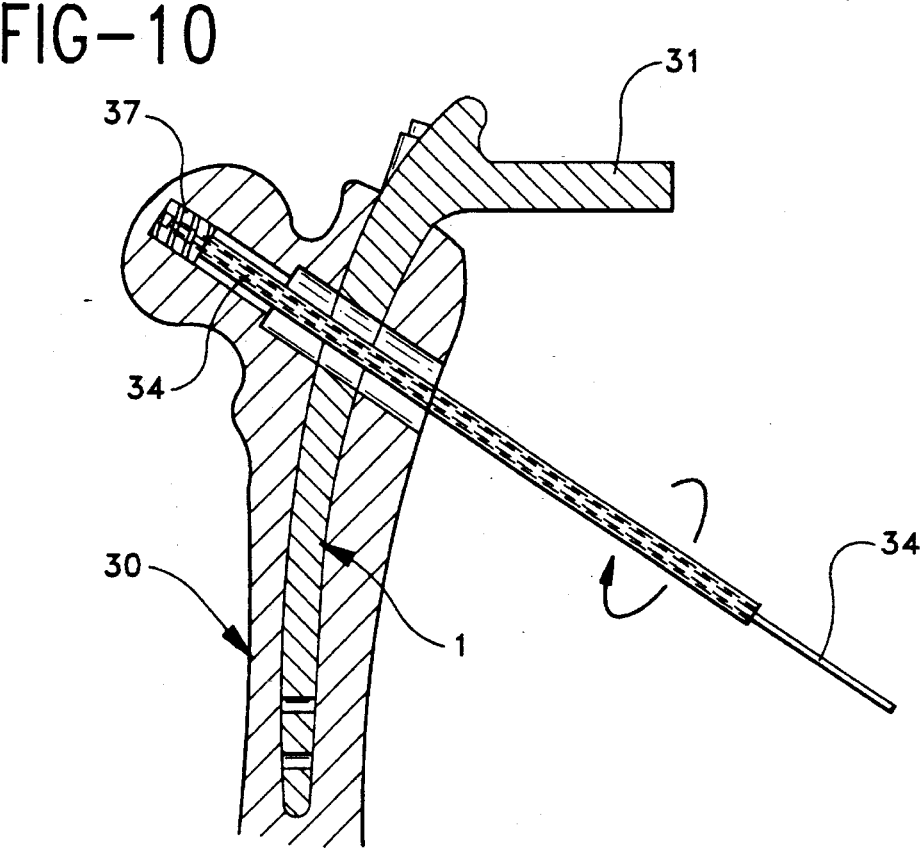
Figure 11:
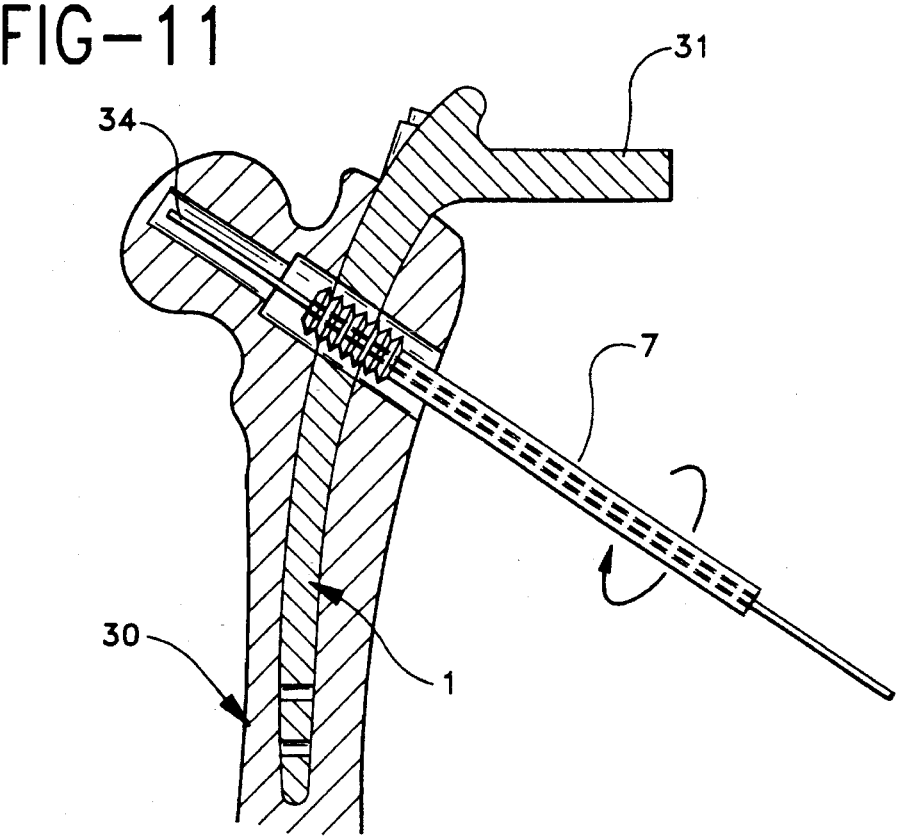

FIG. 8 shows how a 12 mm diameter taper nose drift 36 is driven through the lateral cortex and the rod. The rod and guide wire 34 hunt to allow the drift through. A crown drilling or trepanning tool of 12 mm diameter is now used to remove cancellous bone medial to the rod to receive the sleeve 12 of the present construction, as is shown in FIG. 9. FIG. 10 shows how in the next step a standard single diameter drill 37 is now run over guide wire 34 to the minor diameter of the lag thread on screw 7.

This is substantially the same as the shaft 9 of the screw and can be approximately 8 mm in diameter. The lag screw 7 is now introduced on the guide wire 34 as shown in FIG.

11, the rod being allowed to move as the lag thread passes through.

Figure 12:
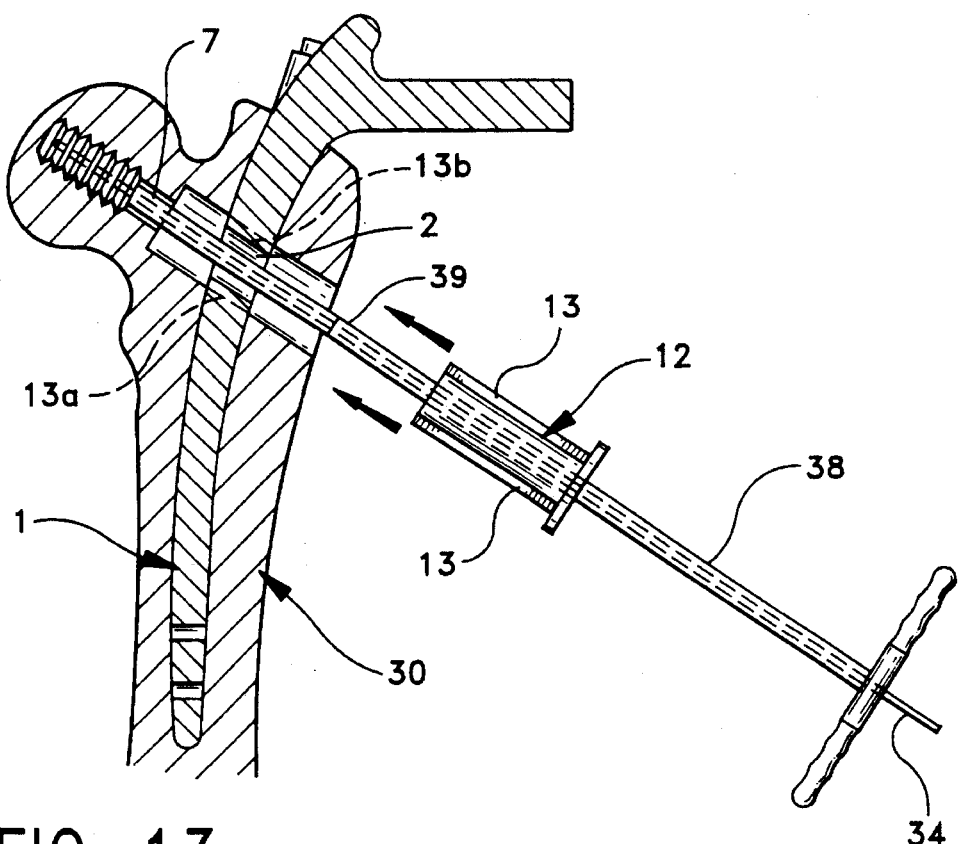

FIG. 12 shows how a sleeve 12 which has previously been placed over a suitable screw driver 38, which has a driving portion 39 which is identical with this section of screw shaft 9, is now moved up the screw driver shaft over shaft 9 of screw 7 and into angulated opening 2. Screw 7 is adjusted by the screw driver 38 to enable the ridges 13 on the sleeve to be located in the appropriate grooves 13a in the bore 2. The screw 7 is now located in position and prevented from rotating in relation to the rod 1.

Figure 13:
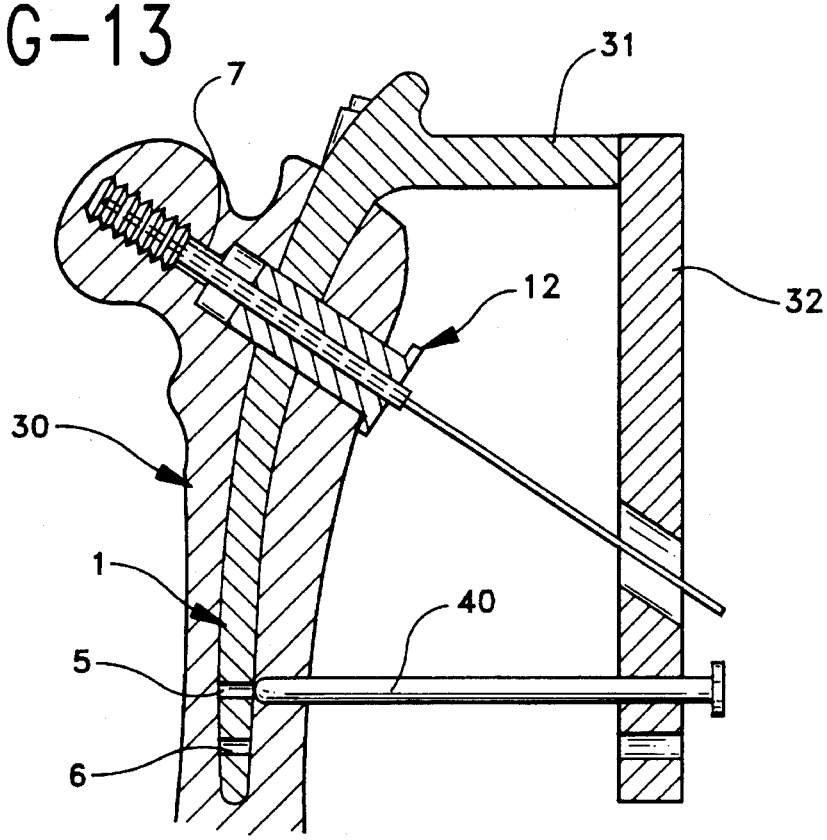

FIG. 13 shows the final stage in which the tunnel guide fitting 32 is replaced on the fitting device 31 and used this time to provide a tunnel locator 40 for drilling through the bone and fitting the distal locking screws through holes 5 and 6 at distal end 4 of the rod.

It will be appreciated that in the fitting process described above that screw 7, although being located against rotation with regard to the rod 1, can move axially. Some surgeons prefer or require this method. If, however, a surgeon wishes to draw threaded end 8 of screw 7 together with the fractured or damaged head of the femur, adjusting screw 19 can be fitted and appropriately rotated by a suitable screw driver to cause the necessary tension.

Figure 3:
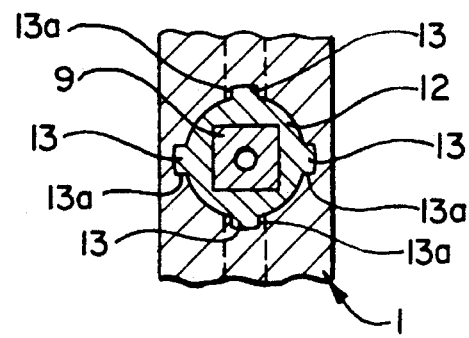
FIG. 3 is a cross-sectional view similar to FIG. 2 but showing an alternative construction.
Figure 4:
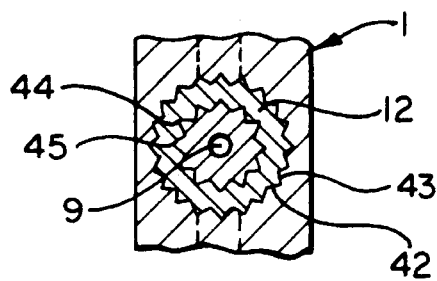
FIG. 4 is a view similar to FIG. 2 but showing another alternative construction.
Figure 5:
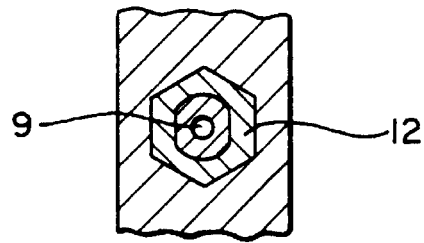
FIG. 5 is a view similar to FIG. 2 but showing yet another alternative construction.

In the construction shown in FIGS. 1 and 2, only two alternative position of the sleeve 12 are provided for angulated opening 2, but it may be desirable to allow for greater flexibility of relative rotation positions either by providing more positions for the sleeve in rod 1, and/or by providing more relative location positions between screw 7 and sleeve 12. FIGS. 3, 4 and 5 show alternative constructions to achieve these aims. In FIG. 3, four ridges 13 are provided on sleeve 12, appropriate grooves 13a being formed in the opening 2. This figure also shows how shank 9 of screw 7 can be of square cross-section to allow alternative positions.

In FIG. 4, the outer surface of sleeve 12 and the inner surface of opening 2 are both provided with splines 42, 43 to enable a number of positions to be chosen and similarly, the bore of sleeve 12 and the outer surface of shank 9 of screw 7 are provided with splines 44, 45, which act in a similar manner.

In the construction shown in FIG. 5 and which is particularly advantageous, bore 2 is hexagon shaped as is the outer surface of sleeve 12 to thus allow six different positions. The interlocking shapes of shank 9 and inner bore of sleeve 12 are shown to be similar to the construction shown in FIGS. 1 and 2, but any other convenient arrangement of shapes could be used.

While several examples of the present invention have been described, it is obvious that many changes and modifications may be made thereunto, without departing from the spirit and scope of the invention.

I claim:

1. An intramedullary intertrochanteric fracture fixation device comprising:
    (a) a femoral neck screw having a shank and a proximal end with a threaded portion of diameter D;
    (b) an intramedullary rod having an angulated opening having a wall therewithin for receiving said femoral neck screw; and
    (c) locking means which is a sleeve which is shaped to locate circumferentially on the shank of said screw and in said angulated opening, but which permits free axial movement between said shank and said sleeve, and which sleeve can slide over said screw shank and within said angular opening and which acts between said femoral neck screw and said wall of said angulated opening so as to prevent relative rotation between said femoral neck screw and said intramedullary rod and including also a tension adjuster for applying an adjustable tension to said neck screw to urge the proximal end of the neck screw towards the rod;

wherein said shank of said neck screw has a diameter which is less than said diameter D and wherein said shank has a longitudinal opening therethrough adapted to receive a guide wire;

wherein said rod has at least two openings which provide alternative relative rotational positions for said neck screw;

wherein said sleeve has an inner bore, the wall of which is shaped to provide first abutment surfaces which engage cooperating surfaces provided on the shank of said neck screw, and the outer surface of said sleeve is provided with second abutment surfaces to engage cooperating surfaces provided on the wall of the angulated opening in said intramedullary rod to prevent relative rotation between said neck screw and said rod;

wherein the cross-section of the outer surface of the sleeve is substantially the same as the cross-section of the opening in the rod, and the cross-section of the inner bore of the sleeve is substantially the same as the cross-section of the shank of the neck screw; and wherein the first abutment surfaces are provided by grooves or ridges on the inner wall of the sleeve.

2. The device according to claim 1 wherein said first abutment surfaces are provided by flats on the wall of the inner bore of the sleeve.

3. The device according to claim 1 wherein the inner bore of the sleeve has a cross-section which is substantially in the shape of a regular polygon.

4. The device according to claim 3 wherein the second abutment surfaces are provided by grooves or ridges on the outer surface of the sleeve.

5. The device according to claim 3 wherein said second abutment surfaces are provided by flats on the outer surface of the sleeve.

6. The device according to claim 5 wherein the outer surface of the sleeve is substantially in the shape of a regular polygon.

7. The device according to claim 6 wherein said tension adjuster includes adjustable means acting on the screw and bearing against the locking member.

8. The device according to claim 1 wherein the intramedullary rod includes means for attaching a removable fitting device.

9. An intramedullary interochanteric fracture fixation device comprising:
    an intramedullary rod having an angulated opening having a wall therewithin for receiving a femoral neck screw having a shank and a proximal end with a threaded portion of diameter D; and locking means which acts between said femoral neck screw and said wall of said angulated opening so as to prevent relative rotation between said femoral neck screw and said intramedullary rod, and including also a tension adjuster for applying an adjustable tension to said neck screw to urge the proximal end of the neck screw towards the rod, wherein said shank of said neck screw has a diameter which is less than said diameter D and wherein said shank has a longitudinal opening therethrough adapted to receive a guide wire, wherein said rod has at least two openings which provide alternative relative rotational positions for said neck screw, wherein said locking means comprises a locking member which is shaped to locate circumferentially on the shank of said screw and in said angulated opening, but which permits free axial movement between said shank and said locking member, wherein said locking member is provided by a sleeve which can slide over said screw shank and within said angulated opening, wherein said sleeve has an inner bore, the wall of which is shaped to provide first abutment surfaces which engage cooperating surfaces provided on the shank of said neck screw, and the outer surface of said sleeve is provided with second abutment surfaces to engage cooperating surfaces provided on the wall of the angulated opening in said intramedullary rod to prevent relative rotation between said neck screw and said rod, wherein the cross-section of the outer surface of the sleeve is substantially the same as the cross-section of the opening in the rod, and the cross-section of the inner bore of the sleeve is substantially the same as the cross-section of the shank of the neck screw, wherein the first abutment surfaces are provided by grooves or ridges on the inner wall of the sleeve, and wherein the inner wall of the sleeve is splined.

10. An intramedullary interochanteric fracture fixation device comprising:

an intramedullary rod having an angulated opening having a wall therewithin for receiving a femoral neck screw having a shank and a proximal end with a threaded portion of diameter D; and locking means which acts between said femoral neck screw and said wall of said angulated opening so as to prevent relative rotation between said femoral neck screw and said intramedullary rod, and including also a tension adjuster for applying an adjustable tension to said neck screw to urge the proximal end of the neck screw towards the rod, wherein said shank of said neck screw has a diameter which is less than said diameter D and wherein said shank has a longitudinal opening therethrough adapted to receive a guide wire, wherein said rod has at least two openings which provide alternative relative rotational positions for said neck screw, wherein said locking means comprises a locking member which is shaped to locate circumferentially on the shank of said screw and in said angulated opening, but which permits free axial movement between said shank and said locking member, wherein said locking member is provided by a sleeve which can slide over said screw shank and within said angulated opening, wherein said sleeve has an inner bore, the wall of which is shaped to provide first abutment surfaces which engage cooperating surfaces provided on the shank of said neck screw, and the outer surface of said sleeve is provided with second abutment surfaces to engage cooperating surfaces provided on the wall of the angulated opening in said intramedullary rod to prevent relative rotation between said neck screw and said rod, wherein the cross-section of the outer surface of the sleeve is substantially the same as the cross-section of the opening in the rod, and the cross-section of the inner bore of the sleeve is substantially the same as the cross-section of the shank of the neck screw, wherein the first abutment surfaces are provided by grooves or ridges on the inner wall of the sleeve, wherein the inner bore of the sleeve has a cross-section which is substantially in the shape of a regular polygon, wherein the second abutment surfaces are provided by grooves or ridges on the outer surface of the sleeve, and wherein the outer surface of the sleeve is splined.

\* \* \* \* \*